US00PP26603P2

(12) United States Plant Patent
Hansen

(10) Patent No.: US PP26,603 P2
(45) Date of Patent: Apr. 12, 2016

(54) ***VERONICA* PLANT NAMED 'ENCHANTED INDIGO'**

(50) Latin Name: *Veronica spicata*
Varietal Denomination: Enchanted Indigo

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 104 days.

(21) Appl. No.: 14/120,594

(22) Filed: Jun. 6, 2014

(51) Int. Cl.
*A01H 5/02* (2006.01)

(52) U.S. Cl.
USPC ..... Plt./251

(58) Field of Classification Search
USPC ..... Plt./251
See application file for complete search history.

*Primary Examiner* — Susan McCormick Ewoldt

(57) ABSTRACT

The new and distinct cultivar of ornamental Spiked Speedwell plant. *Veronica spicata* 'Enchanted Indigo', as herein described and illustrated, with compact habit with stiff upright to branched spikes producing royal-purple flowers over a long period beginning early summer and continuing to early fall with deadheading.

1 Drawing Sheet

Botanical classification: *Veronica spicata.*
Variety denomination: 'Enchanted Indigo'.

BACKGROUND OF THE INVENTION

The present invention relates to the new and distinct cultivar of Spiked Speedwell, botanically known as *Veronica spicata* 'Enchanted Indigo', and hereinafter also referred to by the cultivar name 'Enchanted Indigo' or "the new plant". The new plant originally discovered by the inventor, Hans A. Hansen in the summer of 2010 as a volunteer seedling in a production field block near some plantings of other unknown cultivars the previous season. The specific field block was in Zeeland, Mich., USA and was operated by a wholesale perennial nursery in Zeeland, Mich. The new plant was originally given the breeder code "WG ve12-01". The plant has been asexually propagated by shoot tip cuttings at the same nursery in the greenhouses in Zeeland, Mich., with subsequent asexually propagated plants found to be stable and identical to the original selection with all the same traits as the original seedling.

BRIEF SUMMARY OF THE PLANT

*Veronica* 'Enchanted Indigo' is unique from all other Spiked Speedwell known to the inventor. Several other cultivars have blue to purple flowers, but this is the only variety known by the applicant to have the following trait combinations.

The closest comparison varieties are *Veronica* 'Atomic Violet' U.S. Plant Pat. No. 21,780, *Veronica* 'Glory' U.S. Plant Pat. No. 18,932, *Veronica* 'Goodness Grows' (not patented), U.S. Plant Pat. No. 21,780, *Veronica* 'Hocus Pocus' U.S. Plant Pat. No. 23,853 and *Veronica* 'Sunny Border Blue' (not patented). The new plant has flower color that is more royal purple than 'Goodness Grows' or 'Glory', is shorter than 'Sunny Border Blue' Atomic Violet' and 'Glory' and is slightly taller than 'Hocus Pocus'.

TABLE 1

VERONICA COMPARISON

| Cultivar | Petal Color | Scape Height |
|---|---|---|
| 'Atomic Violet' | dark purple-violet | 48 to 50 cm |
| 'Enchanted Indigo' | royal purple | 40 to 46 cm |
| 'Goodness Grows' | blue | 30 to 35 cm |
| 'Hocus Pocus' | vivid violet-purple | 35 to 40 cm |
| 'Glory' | violet-blue | 38 to 46 cm |
| 'Sunny Border Blue' | violet-blue | 45 to 60 cm |

The following are traits of *Veronica* 'Enchanted Indigo' that in combination distinguish it from all other Spiked Speedwell know to the inventor:

1. Compact habit with stiff upright branched spikes above dense mats of foliage.
2. Scapes with numerous flowers of distinctly and uniformly royal purple petals.
3. Branched peduncles with long blooming season.

BRIEF DESCRIPTION OF THE DRAWINGS

The photograph of the new plant demonstrates the overall appearance and unique traits of *Veronica* 'Enchanted Indigo' as a two-year old plant grown in greenhouse. The colors are as accurate as reasonably possible with color reproductions. Variation in ambient light spectrum, source and direction may cause the appearance of minor variation in color.

DETAILED BOTANICAL DESCRIPTION

Figure 1:
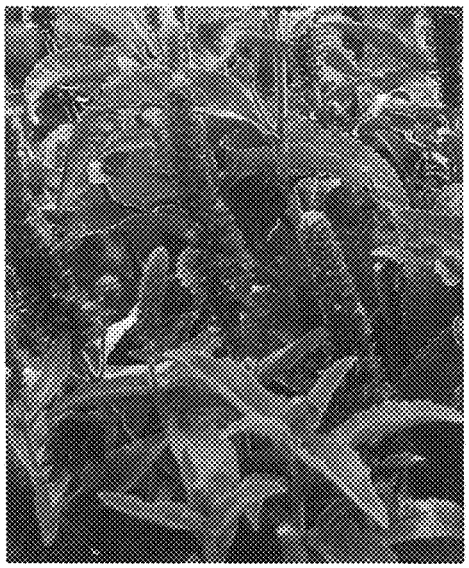
FIG. 1 shows a close-up of the flowers and buds.
Figure 2:
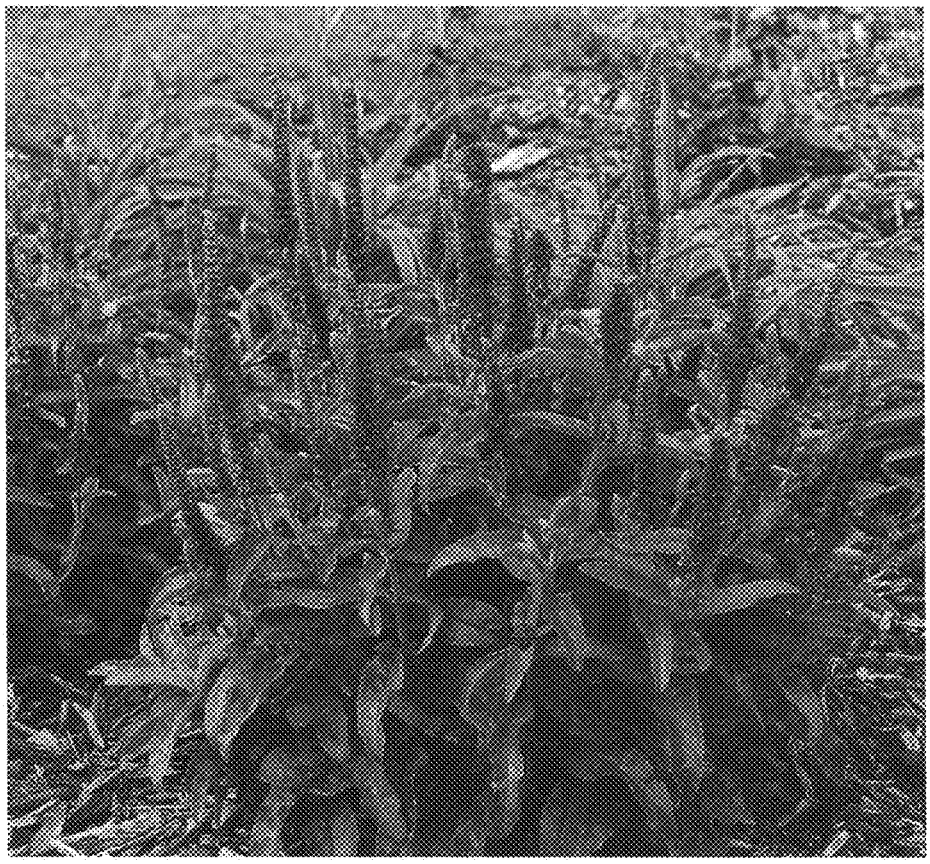
FIG. 2 shows the plant in full flower.

The following descriptions and color references of a greenhouse-grown two-year old plant of *Veronica* 'Enchanted Indigo' are based on the 2001 edition of The Royal Horticultural Society Colour Chart except where common dictionary terms are used. *Veronica* 'Enchanted Indigo' has not been observed under all possible environments. The phenotype may vary slightly with different growing environments such as temperature, light, fertility, soil pH, moisture and maturity levels, but without any change in the genotype. The following observations and size descriptions are based on two-year old plants in the full sun trial garden of a nursery in Zeeland, Mich. with supplemental fertilizer and water as needed.

Botanical classification: *Veronica spicata.*

Parentage: Female (seed parent) unknown *Veronica*; male (pollen parent) unknown.

Plant habit: Hardy herbaceous perennial, compact, with average 26 stems, main stems 16 to 22 cm tall without scapes and clumping to 38 to 45 cm wide; flowering beginning late June in Michigan and continuing for about 6 weeks with occasional repeat if deadheaded.

Leaves: Simple, flat, elliptic to lanceolate, opposite, serrated, minutely pubescent below and above, acute apex, attenuate base; about 8.0 cm long by 3.0 cm wide decreasing in both length and width distally.

Leaf color: Mature leaves nearer RHS 139A than RHS 139B on top, between RHS 138A and RHS 137C below; young expanding leaves nearest RHS 144A above and below.

Veins: Reticulate, minutely and sparsely pubescent below and above; main vein about 1.0 mm diameter at abaxial base and 0.5 mm at adaxial base.

Vein color: Adaxial surface base of center vein nearest RHS 144A, gradually darkening within proximal one third to same color as leaf; on abaxial surface proximal one half of center vein and secondary veins closest to center vein on abaxial surface between RHS 145A and RHS 145B gradually becoming same color as surrounding tissue going toward margin and apex.

Petiole: Simple, concaved upward on edges, minutely pubescent above and below; about 1.0 to 2.0 cm long (distally shorter) and 2.0 mm wide.

Petiole color: Adaxial side nearest RHS 144A in center and RHS 138A on margins; abaxial side between RHS 145A and RNS 145B in center and nearest RHS 138B on margins;

Buds two days prior to opening: Convolute, narrowly oblong, obtuse apex; about 6.0 mm long and 2.5 mm diameter.

Bud color: Nearest RHS 93A throughout.

Flowers: On heavily branched upright spikes in compressed conglomerate; numerous, approximately 220 per main spike; about 8.0 mm in diameter and about 10.0 mm deep; no deductible fragrance; flowers persist individually for 4 to 6 days whether on the plant or cut; petals self-cleaning, sepals persistent.

Petals: Four, coarsely sinuous; one larger petal above and three slightly small below, simple, entire, with rounded apex and fused in basal one third; larger petal about 7.0 mm long by 5.0 mm wide, smaller petals about 7.0 mm long and 4.0 mm wide; glabrous outer and inner sides except with 1.0 mm long hairs at inside tube base.

Flower timing: Early to mid-summer and repeating if deadheaded into early fall.

Flower fragrance: None detected.

Petal color: Inside surface apex between RHS 93A and RHS 90A and lightening to RHS 90C at base, hairs inside tube white, whiter than RHS 155D; outer surface nearest RHS 90A.

Androecium:

*Filaments*.—Two, fused to lower portion of petal; about 6.0 mm long by 0.3 mm; color nearest RHS 90A.

*Anther*.—Dorsifixed, longitudinal; elliptic with acute apex, about 1.5 mm by 1.0 mm; color between RHS N186A and RHS N92A.

*Pollen*.—Abundant, globose, less than 0.1 mm; nearest RHS 4C.

Gynoecium: One, persists after petal drop.

*Style*.—Straight; extending in an angle of about 10 to 40 degrees above horizontal; about 8.0 mm long by 0.3 mm; color nearest RHS N87C in proximal 1.0 mm and darkening to nearest RHS 93A distally.

*Stigma*.—Globose; about 0.25 mm in diameter; color RHS 93A.

*Ovary*.—Spherical to slightly elliptic; about 1.0 mm in diameter; color between RHS 144A and RHS 144B.

Sepals: Four, surface dull, ovate to narrowly ovate, acute apex, base fused forming corolla, sparsely pubescent with minute glandular hairs, upper pair about 3.0 mm long and 2.0 mm wide, lower pair about 4.0 mm long by about 2.0 mm wide.

Sepal color: Abaxial nearest RHS 138A distally and RHS 138B proximally; adaxial nearest RHS 137A throughout.

Peduncle: About 26 per plant; raceme, strong, erect, branched at nodes, round in cross section, minutely pubescent to canescent; about 46 cm long and 3.5 mm in diameter at the base, terminal flowering section of the main stem 18 to 23 cm long, averaging 20 cm long; diameter of flowering portion of raceme about 3.0 cm; freely branching at nearly every node; about 7 to 8 nodes before flowers; average internode length about 3.2 cm.

Peduncle color: Nearest RHS 138B.

Pedicel: Rigid, about 1.0 mm long and 0.5 mm wide, sparsely pubescent with minute hairs to about 45 degrees above horizontal.

Pedicel color: Nearest RHS 137C.

Bract: One, subtending each flower, linear, acute apex, mostly entire, sessile, based fused to peduncle, proximal bracts about 2.5 cm long and 5.0 mm wide and decreasing distally to about 4.0 mm long and less than 1.0 mm wide.

Bract color: Between RHS 137A and RHS 139A above and between RHS 137C and RHS 18A below.

Fruit: Elliptic, about 1.0 mm long; color between RHS 166A and RHS 166B.

Propagation: The plant roots from cuttings in about 2 weeks and finishes to flowering in a 3.8 liter container in 8 to 10 weeks following a vernalization period of about 8 weeks.

Hardiness, pest and disease resistance: The plant grows best with plenty of moisture and adequate drainage, but is able to tolerate some drought when mature. Hardiness at least from USDA zone 4 through 8. Disease and pest resistance beyond what is typical of that of other Spiked Speedwell has not been observed.

I claim:

1. A new and distinct cultivar of ornamental Spiked Speedwell plant, *Veronica spicata* 'Enchanted Indigo', as herein described and illustrated, with compact habit with stiff upright to branched spikes producing royal-purple flowers over a long period and suitable as a potted plant, for the garden, and for cut flower arrangements.

* * * * *